US012778423B2

(12) United States Patent
White et al.

(10) Patent No.: US 12,778,423 B2
(45) Date of Patent: Nov. 3, 2026

(54) LIVING SUBJECT IDENTIFICATION USING IMAGE/VIDEO DISCRIMINATOR FOR RADAR SYSTEMS

(71) Applicant: Innovative Health Monitoring LLC, Stamford, CT (US)

(72) Inventors: Eric Gregory White, Tinton Falls, NJ (US); David Robert Abrams, Aberdeen, NJ (US)

(73) Assignee: Innovative Health Monitoring LLC, Stamford, CT (US)

( * ) Notice: Subject to any disclaimer, the term of this patent is extended or adjusted under 35 U.S.C. 154(b) by 134 days.

(21) Appl. No.: 17/887,426

(22) Filed: Aug. 13, 2022

(65) Prior Publication Data

US 2023/0085640 A1 Mar. 23, 2023

Related U.S. Application Data

(63) Continuation of application No. 17/872,952, filed on Jul. 25, 2022.

(60) Provisional application No. 63/233,388, filed on Aug. 16, 2021, provisional application No. 63/226,703, filed on Jul. 28, 2021.

(51) Int. Cl.
*A61B 5/00* (2006.01)
*A61B 5/01* (2006.01)
*A61B 5/05* (2021.01)

(52) U.S. Cl.
CPC ............ *A61B 5/0035* (2013.01); *A61B 5/015* (2013.01); *A61B 5/05* (2013.01); *A61B 2503/04* (2013.01)

(58) Field of Classification Search
None
See application file for complete search history.

(56) References Cited

U.S. PATENT DOCUMENTS

2006/0025672 A1* 2/2006 Sendai .................. A61B 6/542 600/407
2008/0045847 A1 2/2008 Farag et al.
2008/0119716 A1* 5/2008 Boric-Lubecke .... A61B 5/7225 600/407
2008/0142713 A1 6/2008 Breed et al.
2010/0152600 A1* 6/2010 Droitcour ............ A61B 5/7221 600/534
2014/0023235 A1 1/2014 Cennini et al.
2014/0058256 A1 2/2014 De Jong
2014/0326888 A1 11/2014 Barlow et al.
2015/0078642 A1 3/2015 Fang (Continued)

OTHER PUBLICATIONS

International Search Report and Written Opinion for PCT Application PCT/US2022/038214, mailed on Oct. 12, 2022.

(Continued)

*Primary Examiner* — Christopher Koharski
*Assistant Examiner* — Farouk A Bruce
(74) *Attorney, Agent, or Firm* — Greenberg Traurig, LLP

(57) ABSTRACT

A method and system for presence and vitals detection of a living subject is disclosed herein. The system comprises a device that monitors and is an interface. The device comprises an RGB/IR imaging sensor, a radar, a processor, and a first communication module. The processor is configured to run an algorithm to perform digital signal processing on data provided by the radar and the RGB/IR imaging sensor to generate presence and vitals information for the living subject for communication to the device.

19 Claims, 5 Drawing Sheets

(56) References Cited

U.S. PATENT DOCUMENTS

| | | | | |
|---|---|---|---|---|
| 2015/0097768 | A1* | 4/2015 | Holz | G02B 5/04 348/47 |
| 2016/0151603 | A1 | 6/2016 | Shouldice et al. | |
| 2017/0215772 | A1* | 8/2017 | Garn | A61B 5/08 |
| 2017/0303830 | A1 | 10/2017 | Klein et al. | |
| 2017/0319114 | A1 | 11/2017 | Kaestle | |
| 2018/0049669 | A1* | 2/2018 | Vu | A61B 5/0507 |
| 2018/0053393 | A1 | 2/2018 | White et al. | |
| 2018/0263502 | A1 | 9/2018 | Lin et al. | |
| 2018/0279885 | A1 | 10/2018 | Bulut | |
| 2019/0000391 | A1 | 1/2019 | De Haan et al. | |
| 2019/0139389 | A1 | 5/2019 | White et al. | |
| 2019/0205655 | A1 | 7/2019 | Matsuoka et al. | |
| 2020/0022628 | A1 | 1/2020 | Tao et al. | |
| 2020/0265602 | A1 | 8/2020 | Ostadabbas et al. | |
| 2020/0345274 | A1 | 11/2020 | Ghoshal et al. | |
| 2021/0181307 | A1 | 6/2021 | Ghaffari Ni et al. | |
| 2021/0228083 | A1* | 7/2021 | Strasfeld | G16H 20/10 |
| 2022/0007950 | A1* | 1/2022 | Lev | A61B 5/7267 |

OTHER PUBLICATIONS

International Search Report and Written Opinion for PCT Application PCT/US2022/040235, mailed on Nov. 3, 2022.

International Search Report and Written Opinion for PCT Application PCT/US2022/042515, mailed on Jan. 4, 2023.

Nternational Search Report and Written Opinion for PCT Application PCT/US2022/050257, mailed on Feb. 28, 2023.

* cited by examiner

LIVING SUBJECT IDENTIFICATION USING IMAGE/VIDEO DISCRIMINATOR FOR RADAR SYSTEMS

CROSS REFERENCES TO RELATED APPLICATIONS

The Present application claims priority to U.S. Provisional Patent Application No. 63/233,388 filed on Aug. 16, 2021, and the Present application is a continuation-in-part application of U.S. patent application Ser. No. 17/872,952, filed on Jul. 25, 2022, which claims priority to U.S. Provisional Patent Application No. 63/226,703, filed on Jul. 28, 2021, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to infant monitors.

Description of the Related Art

The best sensor for contactless detection of vitals of a living subject is radar because of its submillimeter sensitivity and ability to permeate materials such as blankets and clothing. Radar has its own set of problems, however, such as susceptibility to RF reflections, spatial sensitivity limited to aimed antennas which are at least partially sensitive in 4π sr, and low spatial resolution of static objects.

The best sensor for detecting presence of a living subject is a red-green-blue (RGB)/short-wave (SW) infrared (IR) imaging sensor which is able to resolve the image of the target. This sensor can also detect vitals in certain circumstances, however, is not ideal for detecting vital signs due to its inability to directly resolve range motion, susceptibility to becoming occluded by blankets, objects, and clothing, and typically insufficient spatial resolution.

The current market for non-contact vitals monitoring has provided products which rely heavily on camera information to detect not only presence, but also for detecting vitals. These systems are compute-heavy, unreliable and easily fooled, are prone to error in dynamic lighting scenarios, and lack the sensitivity to achieve highly accurate vitals detection.

BRIEF SUMMARY OF THE INVENTION

The best way to mitigate these problems is via the use of a doppler radar (pulsed or CW) to resolve vitals information off of a target identified via a RGB/SW IR imaging sensor. A camera is not fooled by RF reflections and has high spatial resolution enabling algorithms to be designed to identify and locate both static and dynamic objects. Meanwhile, a radar is orders of magnitude more sensitive for detecting vitals compared to a camera.

Under certain circumstances, radar is subject to RF reflections and interference which would obstruct its ability to reliably track vitals. Under certain circumstances, the system can then fall back on video processing for determining both presence and vitals from the target.

One aspect of the present invention is a system for presence and vitals detection of a living subject. The system comprises an RGB/IR imaging sensor, a radar, a processor, and a user interface. The RGB/IR imaging sensor is utilized to detect light reflected by a living subject from ambient or controlled light sources. The radar emits a radiofrequency at a specific frequency, and detects the frequency change of reflections of a plurality of targets which have subtle movements from the living subject. The processor is configured to run an algorithm to perform digital signal processing on data provided by the radar and the IR sensor to generate presence and vitals information for the living subject for communication to the user interface.

Another aspect of the present invention is a system for presence and vitals detection of a living subject. The system comprises a monitoring device and an interface device. The monitoring device comprises an RGB/IR imaging sensor, a radar, a processor, and a first communication module. The interface device comprises a second communication module and a user interface module. The RGB/IR imaging sensor is utilized to detect light reflected by a living subject from ambient or controlled light sources. The radar emits a radiofrequency at a specific frequency, and detects the frequency change of reflections of a plurality of targets which have subtle movements from the living subject. The processor is configured to run an algorithm to perform digital signal processing on data provided by the radar and the RGB/IR imaging sensor to generate presence and vitals information for the living subject for communication to the interface device.

Yet another aspect of the present invention is a method for presence and vitals detection of a living subject. The method includes detecting at an RGB/IR imaging sensor of a monitoring device, light reflected by a living subject from ambient or controlled light sources. The method also includes emitting from a radar emitter of the monitoring device a radiofrequency at a specific frequency, and detecting the frequency change of reflections of a plurality of targets which have subtle movements from the living subject. The method also includes receiving at a processor of the monitoring device the data from the radar and the IR imaging sensor. The method also includes running on the processor an algorithm to perform digital signal processing on the data provided by the radar and the IR imaging sensor to generate presence and vitals information for the living subject. The method also includes communicating from a first communication module of the monitoring device the presence and vitals information for the living subject to a second communication module of an interface device. The method also includes presenting on a user interface module of the interface device the presence and vitals information for the living subject.

Yet another aspect of the present invention is a system for presence and vitals detection of a living subject. The system comprises a device that monitors and is an interface. The device comprises an RGB/IR imaging sensor, a radar, a processor, and a first communication module. The device comprises a second communication module and a user interface module. The RGB/IR imaging sensor is utilized to detect light reflected by a living subject from ambient or controlled light sources. The radar emits a radiofrequency at a specific frequency, and detects the frequency change of reflections of a plurality of targets which have subtle movements from the living subject. The processor is configured to run an algorithm to perform digital signal processing on data provided by the radar and the RGB/IR imaging sensor to generate presence and vitals information for the living subject for communication to the device.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Radar has the sensitivity to detect vitals but for presence detection has low confidence. A camera is able to detect presence with high confidence but does not have the resolution for reliable vitals detection. However, using both radar and a camera, presence and vitals detection with high confidence can be achieved.

An RGB/SW IR imaging sensor is used to detect light reflected by a living subject from ambient (sunlight, room lighting, etc.) or controlled (light bulb, SW IR LED, et.) light sources. A Doppler radar, either pulsed or continuous wave, emits RF at a specific frequency, and detects the frequency change of reflections of targets which have subtle movements caused by the respiration and/or ballistocardiography from a living subject.

The field of view of the imaging sensor and the transmit and receive antenna lobe sensitivity are roughly collocated with similar attitude (azimuth and zenith angle) or their offsets calibrated.

Figure 2:
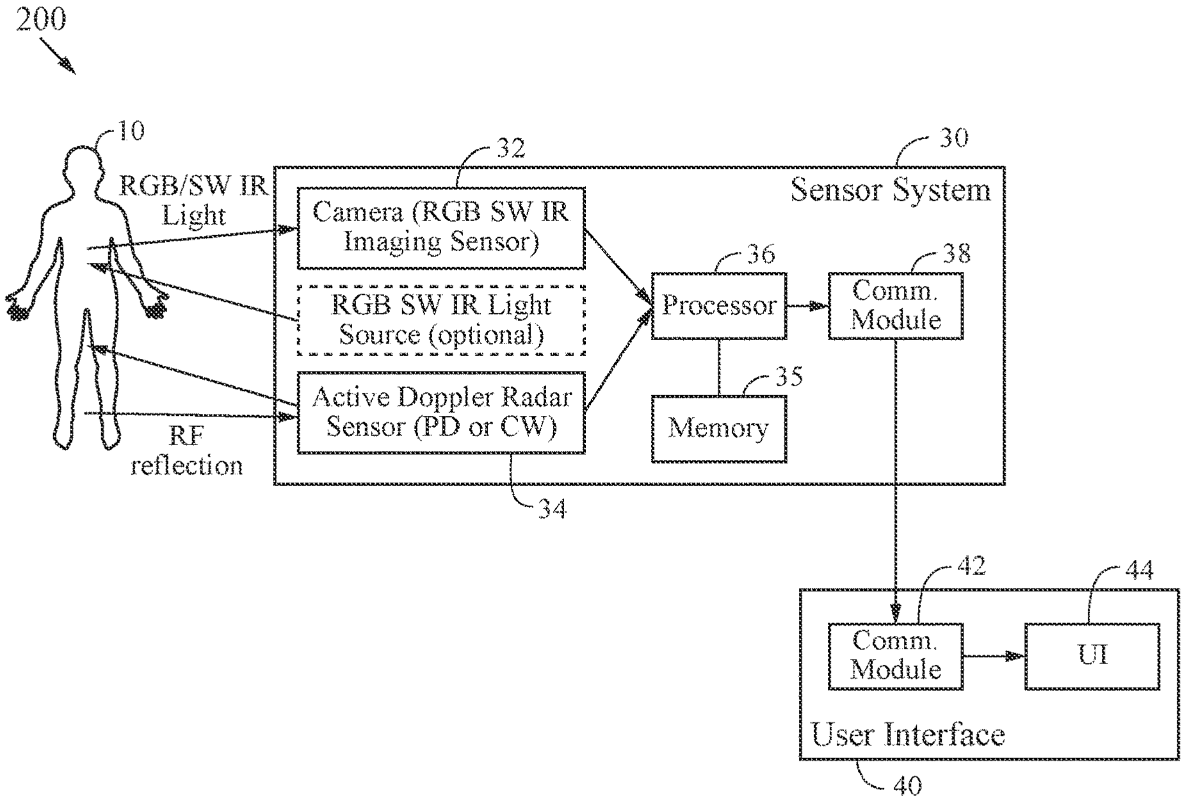
FIG. 2 is a block diagram of one embodiment of a system for presence and vitals detection of a living subject.

As shown in FIG. 2, digital sensor data from these sensor modules are provided for ingestion by a processor unit 36, which runs an algorithm internally to perform digital signal processing, feature extraction, decision logic, and preparation for communication with the user's module 40. Data is then transmitted from the sensor system's 30 communication module 38 to the corresponding user interface system's 40 communication module 42.

A user interface system 40 consists of a communication module 42 which receives data from its corresponding sensor system 30. This data is presented to the user via a user interface 44 such as an LED, a display, a speaker, or any other manner of interface.

An RGB/SW IR imaging sensor determines a presence of a living subject and vitals under certain circumstances. An example commercial product is a Wyze camera, or a Ring camera. A Doppler radar detects the vitals of a living subject by detecting reflected RF. An example commercial product is a Xethru X4.

A compute module 36 with memory 35 and a communication module 38 performs the entirety of presence and vitals detection within the sensing system 30.

A user interface system 40 with communication module 42 receives data and presents information to the user.

The radar vitals detection includes the following: monitor a sensor output with a sample rate S Hz; X=x[n] for CW doppler radar; $X=x_1[i], x_2[i], \ldots x_n[i]$ for pulsed doppler radar with range bins i in Lmin≤i≤Lmax for minimum observed range Lmin and maximum observed range Lmax); S could be 25 Hz, for example; Band pass filter x around vitals frequencies $f_c$; For X, compute discrete Fourier transform Z for a window of time k; k could be 25 seconds, for example; Perform peak-search algorithm on Z and estimate peak level; Example peak search includes argmax; Using peak, estimate noise floor level; Example noise floor estimation includes argmin; Compute SNR[n] by subtracting noise floor from peak; Compare SNR[n] to threshold value b; If SNR[n]>b; Presence verified; Return frequency of peak; Else-Presence disqualified.

The video presence detection includes the following: Collect image I[t] output with sample rate S Hz or when otherwise requested by system; S could be 0.2 Hz for example; Perform classification or object detection model inference using trained model; Example trained model includes AWS Sagemaker Image Classifier ResNet model; Use response from model to update status of baby presence.

A video vitals detection includes the following: Collect image I[t] output with sample rate S Hz or when otherwise requested by system; S could be 25 Hz for example; For each image, compute points of interest using sobel operator; Estimate motion vector, X=x[n], by tracking change in k-means centroids per frame; Band pass filter x around vitals frequencies $f_c$; For X, compute discrete fourier transform Z for a window of time k; k could be 25 seconds, for example; Perform peak-search algorithm on Z and estimate peak level; Example peak search includes argmax; Using peak, estimate noise floor level; Example noise floor estimation includes argmin; Compute SNR[n] by subtracting noise floor from peak; Compare SNR[n] to threshold value b; If SNR[n]>b; Presence verified; Return frequency of peak; Else-Presence disqualified.

Figure 1:
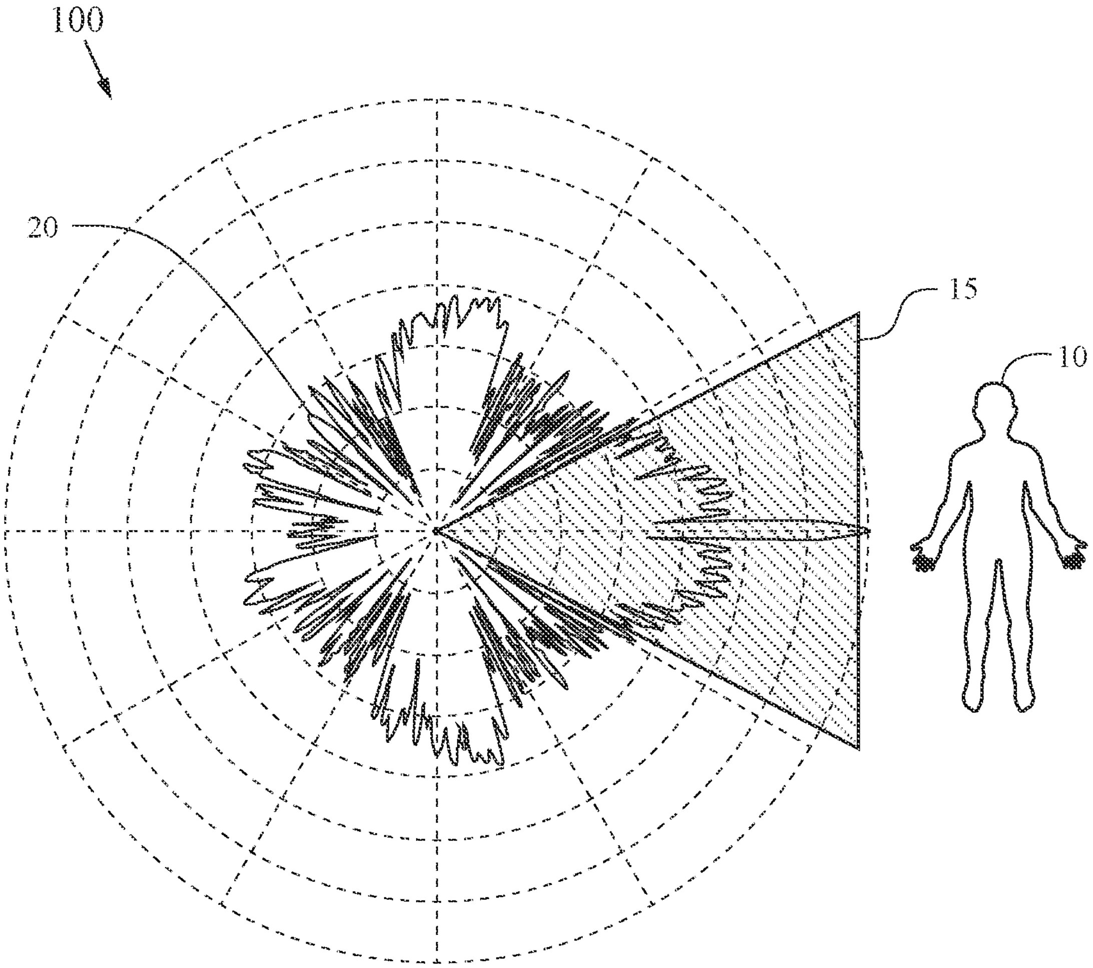
FIG. 1 is an illustration of an antenna pattern.

FIG. 1 is an illustration of an antenna pattern 100 showing the target of interest 10 (the living subject), the camera's field of view 15, and the radar antenna sensitivity pattern 20.

of one embodiment of a system for presence and vitals detection of a living subject FIG. 2 is a block diagram of one embodiment of a system 200 for presence and vitals detection of a living subject. The system 200 comprises an RGB/IR imaging sensor 32, a radar 34, a processor 36, and a user interface 40. The RGB/IR imaging sensor 32 is utilized to detect light reflected by a living subject 10 from ambient or controlled light sources. The radar 34 emits a radiofrequency at a specific frequency, and detects the frequency change of reflections of a plurality of targets, which have subtle movements from the living subject 10. The processor 36 is configured to run an algorithm to perform digital signal processing on data provided by the radar 34 and the IR sensor 32 to generate presence and vitals information for the living subject 10 for communication to the user interface 40.

Figure 3:
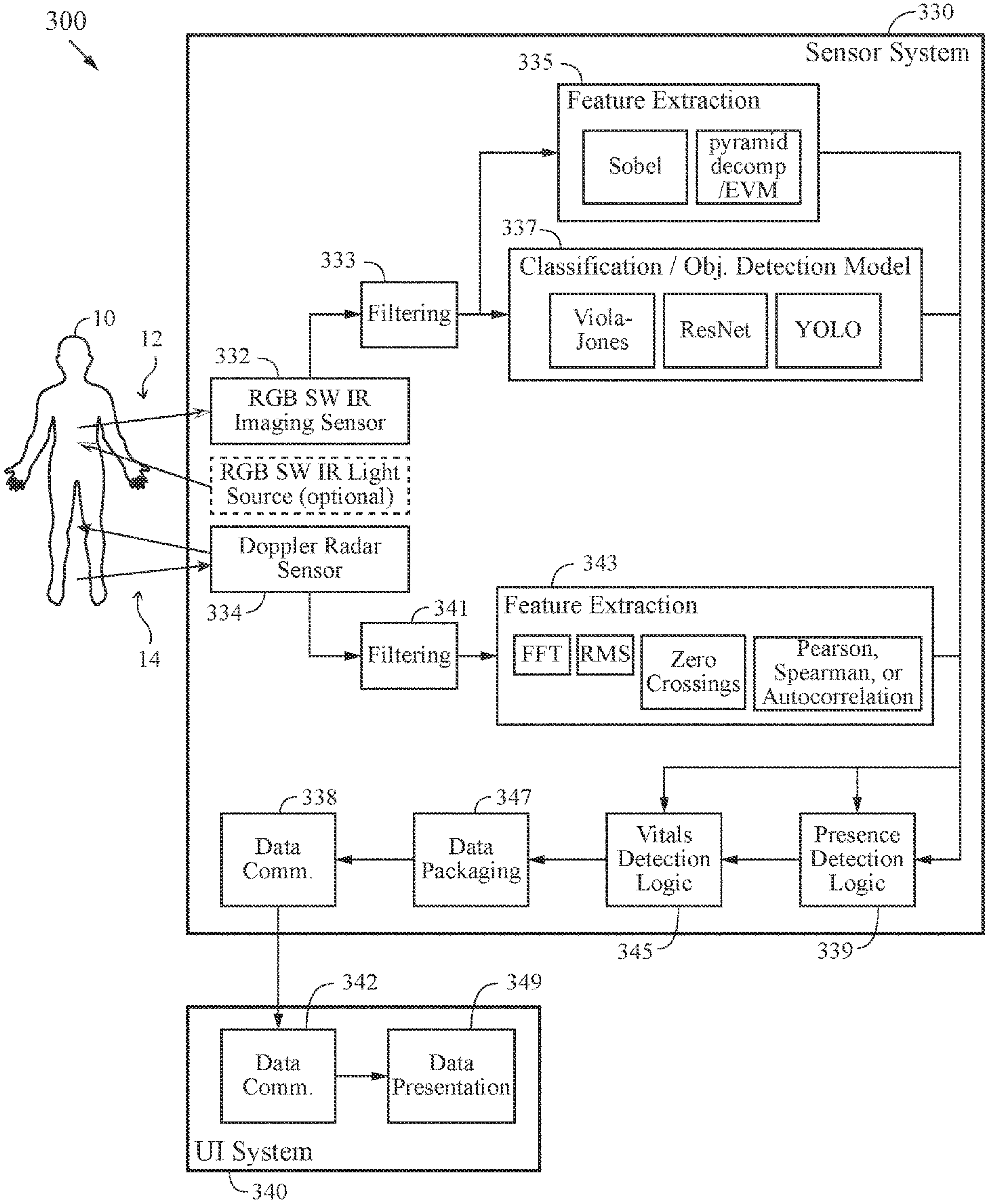
FIG. 3 is a block diagram of a process for presence and vitals detection of a living subject.

FIG. 3 is a block diagram of a process 300 for presence and vitals detection of a living subject. The process includes detecting at an RGB/IR imaging sensor 332 of a monitoring device 330, light reflected 12 by a living subject 10 from ambient or controlled light sources. The process includes filtering 333 the signal and using a feature extraction 335 and an object detection model 337 at a processor, then applying a presence detection logic 339. The process also includes emitting from a radar 334 of the monitoring device 330 a radiofrequency at a specific frequency, and detecting the frequency change of reflections 14 of a plurality of targets which have subtle movements from the living subject 10. The method also includes receiving at a processor of the monitoring device 330 the data from the radar 334, filtering the data 341, applying feature extraction 343 to the data and applying vitals detection logic 345 to the extracted data. The method also includes packaging 347 the data. The method also includes communicating from a first communication module 338 of the monitoring device 330 the presence and vitals data for the living subject 10 to a second communication module 342 of an interface device 340. The method also includes presenting 349 on a user interface module 340 of the interface device 340 the presence and vitals information for the living subject 10.

Figure 4:
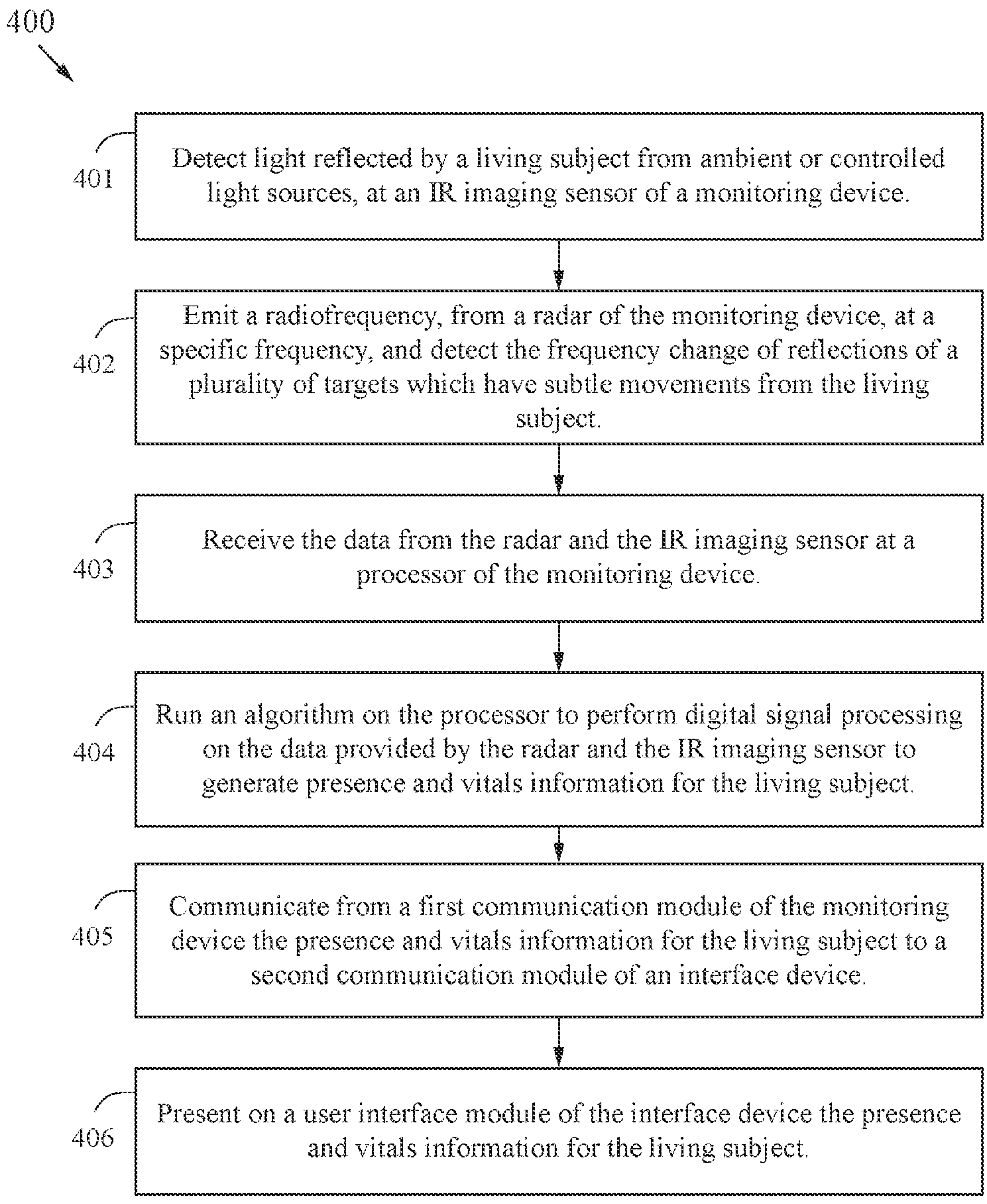
FIG. 4 is a flow chart for a method for presence and vitals detection of a living subject.

FIG. 4 is a flow chart for a method 400 for presence and vitals detection of a living subject. The living subject is an infant, a pet, or an elderly adult. At step 401, light reflected by a living subject from ambient or controlled light sources is detected at an IR imaging sensor of a monitoring device. The IR imaging sensor is preferably an RGB IR imaging sensor. Alternatively, the IR imaging sensor is an SW IR imaging sensor. The radar is a pulsed Doppler radar or a continuous wave Doppler radar.

In step 402, the radar emits a radiofrequency at a specific frequency, and then detects the frequency change of reflections of a plurality of targets which have subtle movements, caused by the respiration and/or ballistocardiography from the living subject.

At step 403, the processor of the monitoring device receives data from the radar and from the IR imaging sensor. Preferably, the monitoring device also comprises a memory configured to store sensor output from the IR imaging sensor. At step 404, the processor runs an algorithm to perform digital signal processing on the data, provided by the radar and by the IR imaging sensor, to generate presence and vitals information for the living subject.

At step 405, a first communication module of the monitoring device communicates the presence and vitals information for the living subject to a second communication module of an interface device. Preferably, both communication modules operate on a WiFi communication protocol, a BLUETOOTH communication protocol, a FM communication protocol, or a FHSS communication protocol.

Finally, at step 406, the presence and vitals information for the living subject is presented on a user interface module of the interface device, preferably using a LED, a display or a speaker.

Figure 5:
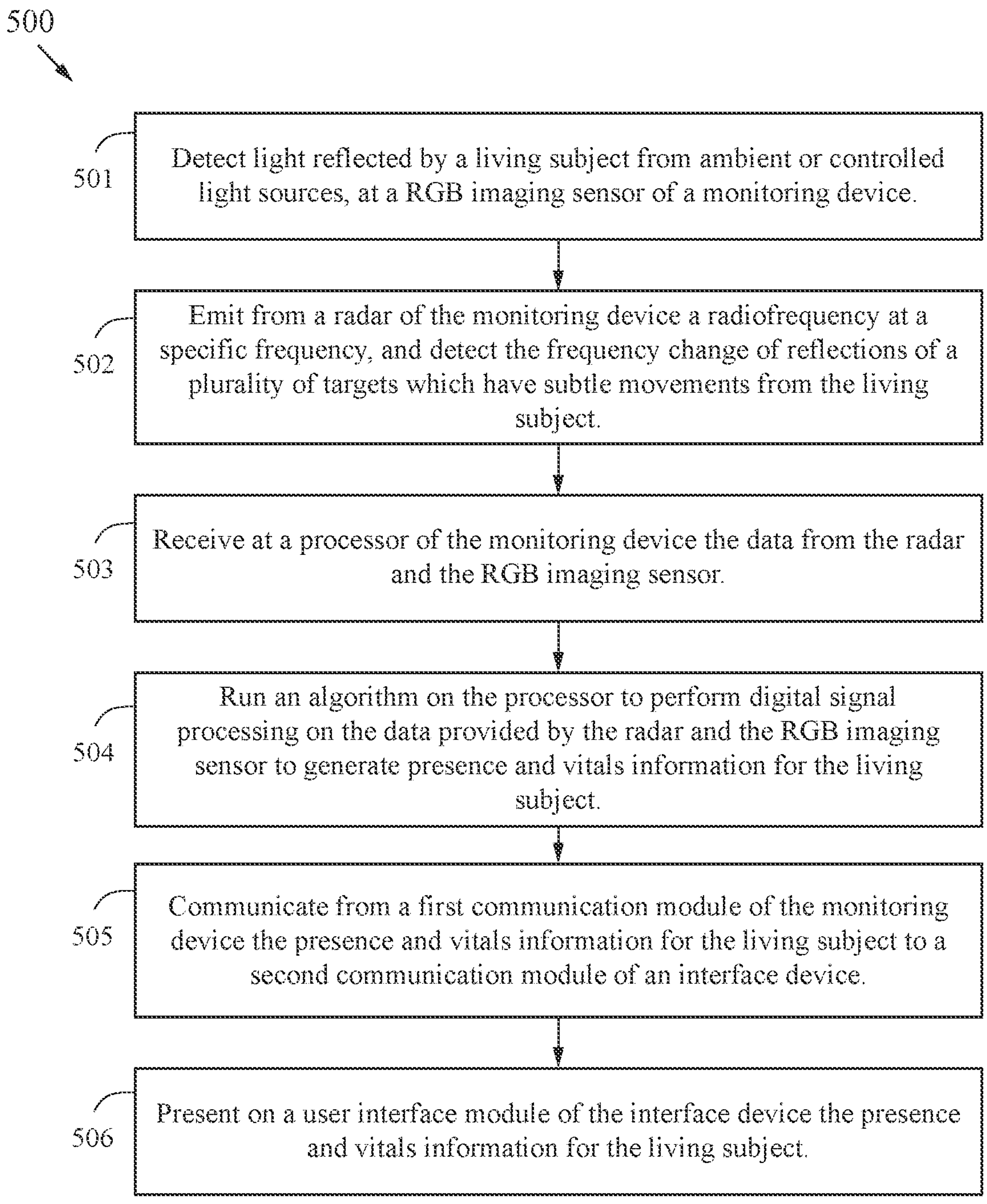
FIG. 5 is a flow chart for a method for presence and vitals detection of a living subject.

FIG. 5 is a flow chart for a method 500 for presence and vitals detection of a living subject. In step 501, light reflected by a living subject from ambient or controlled light sources is detected at a RGB imaging sensor of a monitoring device. In step 502, the radar emits a radiofrequency at a specific frequency, and then detects the frequency change of reflections of a plurality of targets which have subtle movements from the living subject. At step 503, the processor of the monitoring device receives data from the radar and from the RGB imaging sensor. At step 504, the processor runs an algorithm to perform digital signal processing on the data, provided by the radar and by the RGB imaging sensor, to generate presence and vitals information for the living subject. At step 505, a first communication module of the monitoring device communicates the presence and vitals information for the living subject to a second communication module of an interface device. At step 506, the presence and vitals information for the living subject is presented on a user interface module of the interface device.

White et al., U.S. patent Ser. No. 10/825,314 for a Baby Monitor, is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A system for presence and vitals detection of a living subject, the system comprising:
- an infrared (IR) imaging sensor;
- a radar sensor;
- a processor; and
- a user interface;
  - wherein the IR imaging sensor is utilized to detect light reflected by a living subject from ambient or controlled light sources;
  - wherein a radar emitter emits a radiofrequency at a specific frequency, and the radar sensor detects a frequency change of reflections of a plurality of targets which have subtle movements from the living subject;
  - wherein the processor is configured to run an algorithm to perform digital signal processing on data provided by the radar sensor and the IR imaging sensor to:
    - generate, using at least one object detection model trained to detect the living subject in images, presence information comprising an IR imaging-based presence of the living subject based on a detection of the light reflected by the living subject;
      - wherein the presence information comprises identification and location of the living subject;
    - generate, in response to the presence information, vitals information for the living subject based at least in part on:
      - at least one image peak search algorithm for at least one first point of interest, associated with the location of the living subject, identified via a first Sobel operator applied to the light reflected by the living subject and
      - at least one radar peak search algorithm, on a portion of a radar sensitivity pattern associated with the location of the living subject based on the presence information, for at least one second point of interest identified via at least one filter applied to the frequency change of the reflections; and
    - output the vitals information and the presence information for communication to the user interface.

2. The system according to claim 1 wherein the subtle movements are caused by respiration and/or ballistocardiography from the living subject.

3. The system according to claim 1 wherein the radar emitter and the radar sensor are configured for pulsed Doppler radar or continuous wave Doppler radar.

4. The system according to claim 1 wherein the user interface comprises a second communication module for receiving data from a first communication module in communication with the processor.

5. The system according to claim 1 wherein the IR imaging sensor is one of a red-green-blue (RGB) IR imaging sensor or a short-wave (SW) IR imaging sensor.

6. The system according to claim 1 wherein the user interface presents data using a light emitting diode (LED), a display or a speaker.

7. A method for presence and vitals detection of a living subject, the method comprising:

detecting at an infrared (IR) imaging sensor of a monitoring device, light reflected by a living subject from ambient or controlled light sources;

emitting from a radar emitter of the monitoring device a radiofrequency at a specific frequency, and detecting by a radar sensor a frequency change of reflections of a plurality of targets which have subtle movements from the living subject;

receiving, at a processor of the monitoring device, data from the radar sensor and the IR imaging sensor;

running on the processor an algorithm to perform digital signal processing on the data provided by the radar sensor and the IR imaging sensor to:

generate, using at least one object detection model trained to detect the living subject in images, presence information comprising an IR imaging-based presence of the living subject based on a detection of the light reflected by the living subject;

wherein the presence information comprises identification and location of the living subject;

generate, in response to the presence information, vitals information for the living subject based at least in part on:

at least one image peak search algorithm for at least one first point of interest, associated with the location of the living subject, identified via a first Sobel operator applied to the light reflected by the living subject and at least one radar peak search algorithm, on a portion of a radar sensitivity pattern associated with the location of the living subject based on the presence information, for at least one second point of interest identified via at least one filter applied to the frequency change of the reflections; and output the vitals information and the presence information for communication to a user interface;

communicating from a first communication module of the monitoring device the presence and vitals information for the living subject to a second communication module of an interface device; and presenting on a user interface module of the interface device the presence and vitals information for the living subject.

8. The method according to claim 7 wherein the subtle movements are caused by respiration and/or ballistocardiography from the living subject.

9. The method according to claim 7 wherein the radar emitter and the radar sensor are configured for pulsed Doppler radar or continuous wave Doppler radar.

10. The method according to claim 7 wherein the IR imaging sensor is a red-green-blue (RGB) IR imaging sensor or a short-wave (SW) IR imaging sensor.

11. The method according to claim 7 wherein the first communication module and the second communication module operate on a WiFi communication protocol, a BLUETOOTH communication protocol, a frequency modulation (FM) communication protocol, or a frequency hopping spread spectrum (FHSS) communication protocol.

12. A system for presence and vitals detection of a living subject, the system comprising:

a monitoring device comprising an imaging sensor, a radar sensor, a processor, and a first communication module; and an interface device comprising a second communication module and a user interface module;

wherein a red-green-blue (RGB) imaging sensor is utilized to detect light reflected by a living subject from ambient or controlled light sources;

wherein a radar emitter emits a radiofrequency at a specific frequency, and the radar sensor detects a frequency change of reflections of a plurality of targets which have subtle movements from the living subject;

wherein the processor is configured to run an algorithm to perform digital signal processing on data provided by the radar sensor and the RGB imaging sensor to:

generate, using at least one object detection model trained to detect the living subject in images, presence information comprising an RGB imaging-based presence of the living subject based on a detection of the light reflected by the living subject;

wherein the presence information comprises identification and location of the living subject;

generate, in response to the presence information, vitals information for the living subject based at least in part on:

at least one image peak search algorithm for at least one first point of interest, associated with the location of the living subject, identified via a first Sobel operator applied to the light reflected by the living subject and at least one radar peak search algorithm, on a portion of a radar sensitivity pattern associated with the location of the living subject based on the presence information, for at least one second point of interest identified via at least one filter applied to the frequency change of the reflections; and output the vitals information and the presence information for communication to the user interface.

13. The system according to claim 12 further comprising a memory configured to store sensor output from the RGB imaging sensor, the radar sensor, or both.

14. The system according to claim 12 wherein the subtle movements are caused by respiration and/or ballistocardiography from the living subject.

15. The system according to claim 12 wherein the user interface presents data using a light emitting diode (LED), a display or a speaker.

16. The system according to claim 12 wherein the user interface comprises the second communication module for receiving data from the first communication module in communication with the processor.

17. The system according to claim 16 wherein the first communication module and the second communication module operate on a WiFi communication protocol, a BLUETOOTH communication protocol, a frequency modulation (FM) communication protocol, or a frequency hopping spread spectrum (FHSS) communication protocol.

18. The system according to claim 12 wherein the RGB imaging sensor is an RGB infrared (IR) imaging sensor or an RGB short-wave (SW) IR imaging sensor.

19. The system according to claim 12 wherein the radar emitter and the radar sensor are configured for pulsed Doppler radar or continuous wave Doppler radar.

* * * * *